United States Patent [19]

Campbell et al.

[11] Patent Number: 5,140,994
[45] Date of Patent: Aug. 25, 1992

[54] SURFACE VIBRATION ANALYSIS

[75] Inventors: Frederick C. Campbell, Newport-on-Tay; Brian E. Storey, Dundee, both of Scotland

[73] Assignee: National Research Development Corporation, London, United Kingdom

[21] Appl. No.: 630,722

[22] Filed: Dec. 20, 1990

Related U.S. Application Data

[63] Continuation of Ser. No. 372,351, Jun. 20, 1989, abandoned.

[30] Foreign Application Priority Data

Oct. 21, 1987 [GB] United Kingdom ............. 8724687
Oct. 21, 1988 [GB] United Kingdom PCT/GB88/00921

[51] Int. Cl.$^5$ .................... A61B 5/103; A61B 5/11
[52] U.S. Cl. .................... 128/782; 128/780
[58] Field of Search ............ 128/773, 774, 780, 782

[56] References Cited

U.S. PATENT DOCUMENTS

| | | | |
|---|---|---|---|
| 3,695,253 | 10/1972 | Vielhauer | 128/695 |
| 3,985,121 | 10/1976 | Hellenbrand | 128/689 |
| 4,437,473 | 3/1984 | Mollan | 128/773 |
| 4,823,808 | 4/1989 | Clegg et al. | 128/780 |
| 4,836,218 | 6/1989 | Gay et al. | 128/773 |

FOREIGN PATENT DOCUMENTS

| | | | |
|---|---|---|---|
| 8906932 | 8/1989 | PCT Int'l Appl. | 128/773 |
| 0641957 | 1/1979 | U.S.S.R. | 128/773 |

OTHER PUBLICATIONS

Vasseur et al., "Postprandial Bowel Sounds", IEEE Transactions on Bio-Medical Engineering, vol. 22, No. 25, May 1975, pp. 443–448.
Politzer et al., "The Genesis of Bowel Sounds: Influence of Viscus and Gastrointestinal Content", Gastroenterology, vol. 71, No. 2, Aug. 1976, pp. 282–285.

*Primary Examiner*—Lee S. Cohen
*Assistant Examiner*—Krista M. Pfaffle
*Attorney, Agent, or Firm*—Ratner & Prestia

[57] ABSTRACT

A method for determining motility comprising the detection, by means such as a transducer, of vibration of the external abdominal surface generated by gastrointestinal vibration and analysis of the signals produced by the transducer. Means are provided for integrating the signal over discrete time intervals in order to obtain meaningful results.

8 Claims, 6 Drawing Sheets

SURFACE VIBRATION ANALYSIS

This application is a continuation of application Ser. No. 07/372,351 filed June 20, 1989, now abandoned.

BACKGROUND OF THE INVENTION

This invention relates to a method of and apparatus for determining motility.

A sophisticated control system governs the strength and sequence of contractions of the stomach and bowel. The integrity of this control system is vital to ensure that food contents are adequately mixed with the digestive juices and are pushed along the length of the gut at the correct rate to allow adequate digestion and absorption of nutrients. This activity of the stomach and bowel (i.e. the strength and sequence of contractions) is known as its motility. Because the control system is complex, breakdowns occur frequently and disorders of gastrointestinal motility are common. The severity of these disorders varies from that which is uniformly fatal (fortunately uncommon) to that which causes chronic and disabling symptoms.

It has been estimated that approximately 90% of patients who have been referred to any gastrointestinal clinic suffer from some form of motility disorder. In this connection see Loof L., Adani H. O., Agera S.I., et al. the Diagnosis and Therapy Survey (Oct. 1987-March 1983). Health Care consumption and current drug therapy in Sweden. Scand. J. Gastroenterol, 20 (Suppe 109): 29-35 (1985). Although motility disorders are common, they are poorly understood probably because the techniques for their steady are limited. These techniques involve measurement of pressure changes inside the gut, by the swallowing of one or more tubes or radio pressure pills. Since the gastrointestinal tract is 26 feet long, the techniques only provide information at few loci along its length. The techniques are thus difficult and uncomfortable and are suitable only for small numbers of patients at specialist centres.

Contractions of the gastrointestinal tract are associated with the release of vibrational energy, both within and outside the acoustic spectrum. This energy may be captured, measured and analyzed. That which lies within the acoustic spectrum may be detected by a stethoscope as bowel sounds and previous investigators have been concerned only with the capture of bowel sounds. In early studies, sounds were captured over short intervals of time and all characterization of the signal was subjective or qualitative. For example, readers are referred to: 1) Du Plessis, D. J. Clinical observations on intestinal motility, S. Afr. Med J. 28: 27-33 (1954), 2) Wells C., Rawlinson K., Tinckler L., Jones H. and Saunders J. Illeus and postoperative intestinal motility, Llancet 2: 136-137 (1961), 3) Baker L. W. and Dudley H.A.F. Auscultation of the abdomen in surgical patients. Lancet 2: 517-519 (1961), 4) Horn G.E. and Mynors J. M. Recording the bowel sounds. Med & Biol Engin. 205-209 (1955).

Several studies carried out some crude signal analysis, but recording times were short and results inconclusive. See 1) Farrar J. T. and Ingelfinger F. J. Gastrointestinal motility as revealed by a study of abdominal sounds, Gastroenterology 29: 789-800 (1955), 2) Watson W.C. and Know Elizabeth, C. Phonoenterography: the recording and analysis of bowel sounds, Gut 8: 88-94 (1967), 3) Politzer J. P., Devoede E., Vasseur C., et al., the genesis of bowel sounds: influence of viscus and gastrointestinal content, Gastroenterology 71: 282-285 (1976).

All of the previous techniques have relied upon microphones for signal capture, with limited success. Microphones essentially address the acoustic spectrum and in general they depend upon an air interface for conversion of vibrational energy to an electronic signal. Hence, they are sensitive to any other vibrational interference, for example background noise, which is transmitted through air.

SUMMARY OF THE INVENTION

According to the present invention there is provided a method of determining motility comprising contacting an external surface of an abdomen with means for producing a signal in response to vibration of said surface generated by gastrointestinal contractions, detecting said vibrations and thereby producing said signal, and analysing the produced signal in order to detect motility.

Further according to the invention there is provided a method of generating data relating to motility, comprising contacting an external surface of an abdomen with means for producing a signal in response to vibration of said surface, detecting said vibration and thereby producing said signal, and processing said signal to generate data relating to motility.

Preferably the vibration is detected over a frequency range extending beyond the acoustic spectrum, most preferably over the range from 2 to 60,000 Hz.

The signal obtained is preferably filtered to remove elements other than those emanating from the gastrointestinal contractions, for example those from aortic contraction. This can be done by filtering out vibrations of low frequency, for example below 40 Hz. The signal may also be amplified, preferably at fixed gain, and may be stored and/or further processed.

Further according to the present invention there is provided apparatus for use in determining motility, comprising means for producing a signal in response to vibration of a surface generated by gastrointestinal contractions, and means for analyzing a signal produced thereby.

The means for producing the signal is preferably a transducer such as an Accelerometer. Accelerometers have substantial advantages over the microphones used in the prior art, by providing high charge or voltage sensitivity, low acoustic sensitivity, a wide frequency range and a wide dynamic range with high resonance frequency.

Preferably, filter means is provided in conjunction with the transducer to remove from the signal elements corresponding to selected vibration frequencies so that the signal becomes concentrated on those frequencies emanating from the gastrointestinal contractions. It has been found in practice that the wide frequency range of the transducer allows it to detect vibrations emanating from the aorta, and investigation has shown that these aortic vibrations have frequencies below 40 Hz, with peaks at 14 Hz and 21 Hz. The filter means therefore can of advantage prevent further passage of signals representative of such low frequencies, and thereby remove aortic interference.

Preferably also the signal produced corresponds to vibrations over a range extending beyond the acoustic spectrum, most preferably over the frequencies range from 2 to 60,000 Hz.

The application of the transducer to the vibrating abdominal surface provides direct reception of the vibrations by the transducer without the inclusion of an air interface, and this allows a broad range of vibrational frequencies to be monitored without significant interference by external background vibrations.

Amplifier means may be included in the apparatus, preferably a fixed gain amplifier such for example as an impulse level meter. The signal is preferably in the form of an electrical charge of low magnitude. This charge may be converted into a voltage and amplified. Means may also be provided for summing, averaging or integrating the signal over discrete time intervals, and this may be in the form of a digital integrator. Data storage means and/or graphic display means may be included.

The method and apparatus of the invention are applied externally of the body and are therefore non-invasive, which avoids the discomfort associated with previously proposed techniques in which patients were required to swallow pressure pills or tubes. The present invention also allows vibrations from the gut as a whole to be determined, instead of only localised pressure changes within the gut.

BRIEF DESCRIPTION OF THE DRAWING

Embodiments of the invention will now be described by way of example with reference to the accompanying drawings and charts, in which.

DESCRIPTION OF THE PREFERRED EMBODIMENTS

Figure 1:
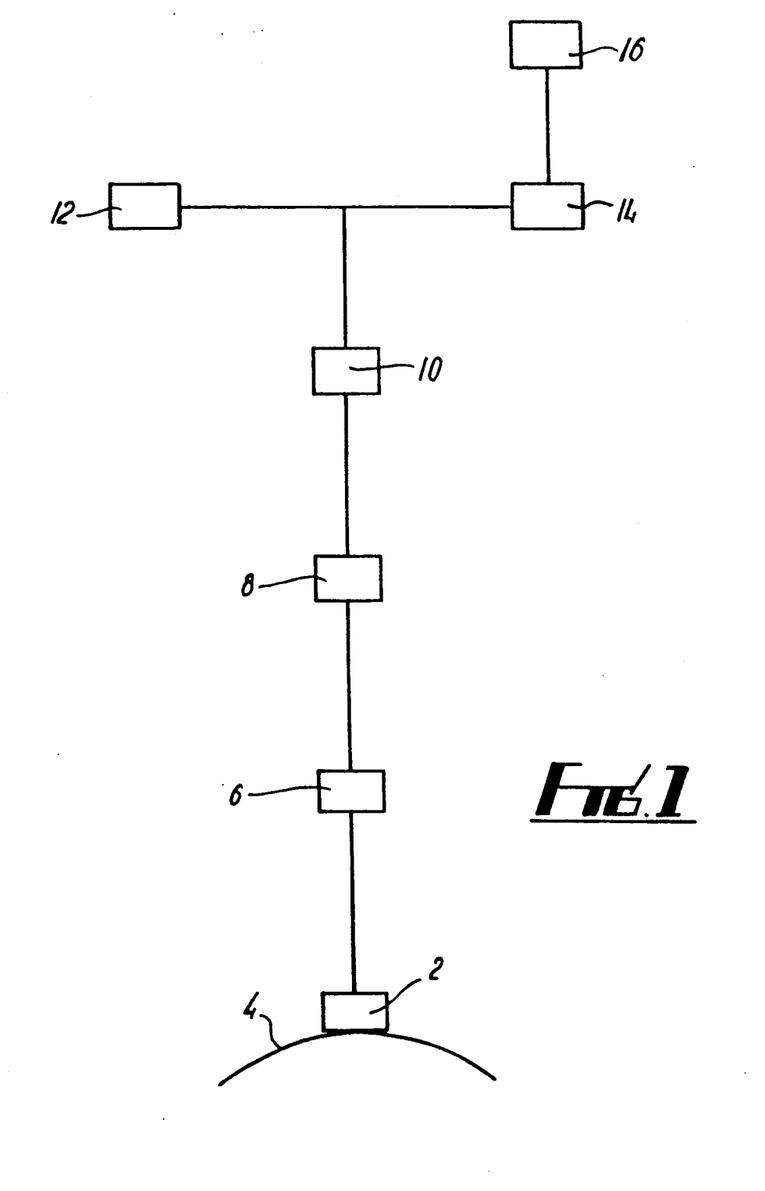
FIG. 1 is a schematic diagram of one form of the apparatus of the present invention.

Referring to FIG. 1, the apparatus of this embodiment of the invention has a piezoelectric electromechanical transducer 2 (in this case a Bruel and Kjaer Type 4370) which is located on the abdomen 4 of a patient and held there by a strap passing round the patient's body (not shown) or by adhesive. The transducer 2 has a frequency response of from 2 to 60,000 Hz.

The transducer produces an electrical signal which passes to a series of hiqh pass filters 6 selected to remove from the signal elements characteristic of the undesired vibrations of the aorta, so as to leave intact the target signals representative of the gastrointestinal contractions. A 4 pole hiqh pass filter is used, having a gain which was flat from 80 to 3000 Hz. Below 80 Hz the signal is attenuated at a rate of 24 dB per octave producing a reduction of 70 dB, i.e. 3000 fold, in signal intensity at 10 Hz. Above 3000 Hz the signals are gradually attenuated to eliminate hiqh frequency electronic noise, resulting in a 10 dB reduction at 20 KHz. While the filter inevitably removes a small portion of the gastrointestinal signal, especially at the lowest frequencies, this is found not to be significant in the overall results.

The filtered signal passes from the filter 6 to a calibrating device 8 in which it is calibrated against fixed oscillator output, and thence to an impulse level meter 10 which amplifies the signal at fixed gain to achieve a sufficiently rap[d electronic response to the constantly changing signal. In the present embodiment a Bruel and Kjaer Type 2626 gains-driven "conditioning" amplifier is used, having selectable input and output sensitivity. This allows the precise sensitivity of the transducer 2 to be fed in, which sets the sensitivity of the amplifier so that the output is calibrated from 0.001 volts/g to 10 volts/g.

The amplified signal is stored on magnetic tape or disc 12, and simultaneously processed by a digital integrator 14 which measures the accumulated signal amplitude in 5-second packets over the entire study interval and also provides numerical values for the signal measurements.

A chart recorder 16 is linked to the integrator 14 to provide graphic display of the results.

The storage means is, in this embodiment, a Uher 4400 Report Monitor which allows off-tape monitoring of the signal during recording. The frequency response of the machine is 20–25,000 Hz at a speed of 7.5 ips with a signal to noise ratio >64 dB. The recorder is calibrated to allow measurement of results; the calibrator produces an amplitude stabilized fixed-frequency signal of 1 KHz which is fed to the recorder for 1 minute in place of the normal input signal at the start of each recording. On replay this signal is measured and the results used to correct for any sensitivity variations.

With a maximum signal frequency of 10,000 Hz accurate processing and measurement of lengthy signals by conventional analogue to digital conversion would require manipulation of vast quantities of data. Indeed, previous work which has addressed the concept of digitization and computerizations of bowel sound energy has been limited by these technical considerations to analysis of very short duration signals, for example 5–20 milliseconds duration, which rendered meaningful interpretation impossible. The digital integrator 14 deals with this problem by a method involving total data integration over set time intervals, for example intervals of 5 seconds although these an be varied at will. This allows accurate digitization of the integrated signal and permitted capture and analysis of long duration signals for evaluation against conventional tests of gastrointestinal activity.

The digital integrator in this case is a purpose designed unit with a linear response extending well outside the required operating range.

The output from the digital integrator, providing the average signal level over each successive 5-second interval, is fed to the chart recorder 16 for display.

The apparatus of this embodiment of the invention can be used for conducting various studies, for example:

1) Studies in the fasting phase.

The results here can detect by a non-invasive technique a parameter which hitherto has only been detectable by having the patient swallow long tubes or radio capsules. This parameter is called migrating motor complex (MMC), which is essentially a rhythmic sequence of bowel activity and quiescence. The MMC is the cornerstone of motility measurements.

2) Studies showing the response to a meal.

At the present time, there is no other way known to the applicants of doing this. However, the gastrointestinal response to a meal is clearly shown and can be measured numerically by the present technique.

3) Studies measuring the effects of drug stimulation of the gastrointestinal tract.

Measurement of drug stimulation is conventionally very difficult and requires the intubation techniques mentioned earlier.

4) Demonstration of the effect of surgery on the bowel.

Immediately after a surgical operation, the stomach and bowel "go to sleep" for a variable interval. This condition is known as "post operative ileus". During this interval, the stomach and bowel are not functioning and consequently, the patient cannot take food or drink by mouth and his recovery after the operation is delayed. Post operative ileus lasts a variable interval, and the present apparatus and method have been used to carry out studies of its duration and to examine the effects of certain drugs on it. With conventional techniques these studies would not be practicable, because of the discomfort that intubation would cause to a patient who is weakened by a recent operation.

5) Diagnosis of chronic intestinal obstruction.

When the bowel becomes completely blocked, the patient becomes acutely ill but the diagnosis is easy. When the obstruction is partial, the patient has chronic and disabling symptoms but the diagnosis is very difficult. Hitherto the only method of diagnosis has been clinical suspicion and confirmation by an operation. In some cases the suspicion is not confirmed and the patient undergoes an unnecessary operation. With the present method and apparatus, the diagnosis of chronic intestinal obstruction is easy, and the hiqh energy peaks with rapid repetition which are obtained on the chart recorder 16 are characteristic.

This system can be used as the basis for development to provide a measurement of signal amplitude, storage of longduration signals and real time data logging which charts energy measurements at one-minute intervals over the whole study period.

Reference is now made to the accompanying charts designated FIGS. 2 to 7 which are the results obtained from the chart recorder such as that of FIG. 1 in examples of the method of the invention.

Figure 2:
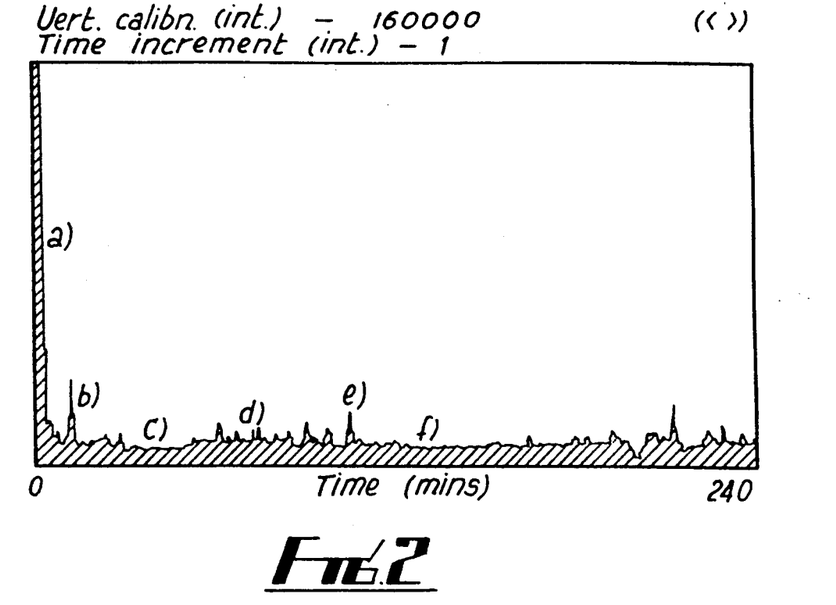
FIGS. 2 to 9 are charts illustrating the results obtained using the apparatus of FIG. 1 on patients, as will be described hereinafter.

FIG. 2—Fasting Phase.

Cyclical peaks of activity interspersed with intervals of quiescence over a 4 hour interval can be clearly seen. The calibration signal (a) is followed by energy leading to peak (b) which in turn is followed by a return to quiescence (c). There is then a gradual energy build up (d), a further peak (e), return to quiescence (f) and repetition of the process. The patterns resemble a Migrating Motor Complex.

Figure 3:
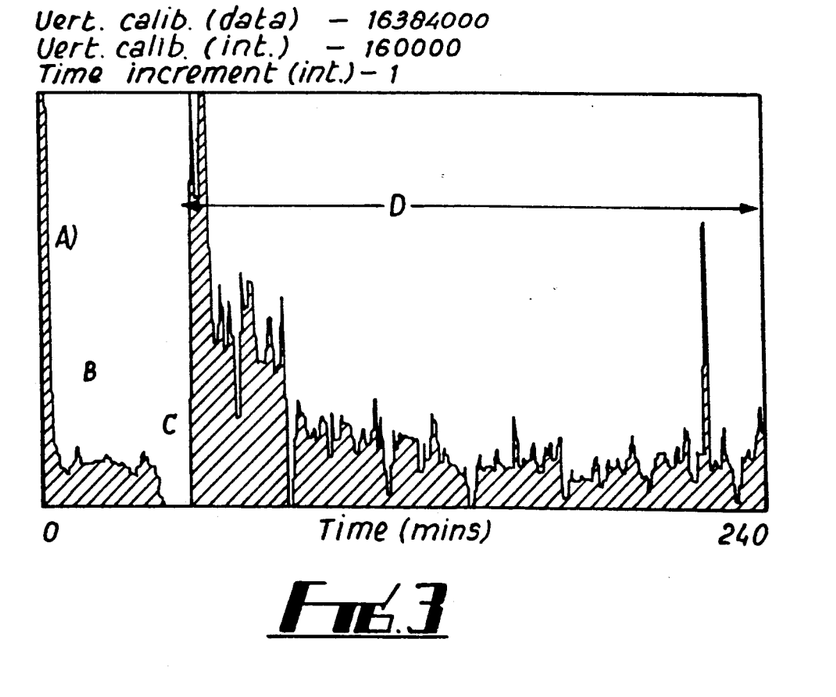

FIG. 3—Response to a Solid Meal.

A represents the calibration signal, B the fasting activity and C an 8-minute pause for a solid meal. At D the gastrointestinal response to the solid meal is clearly shown.

Figure 4:
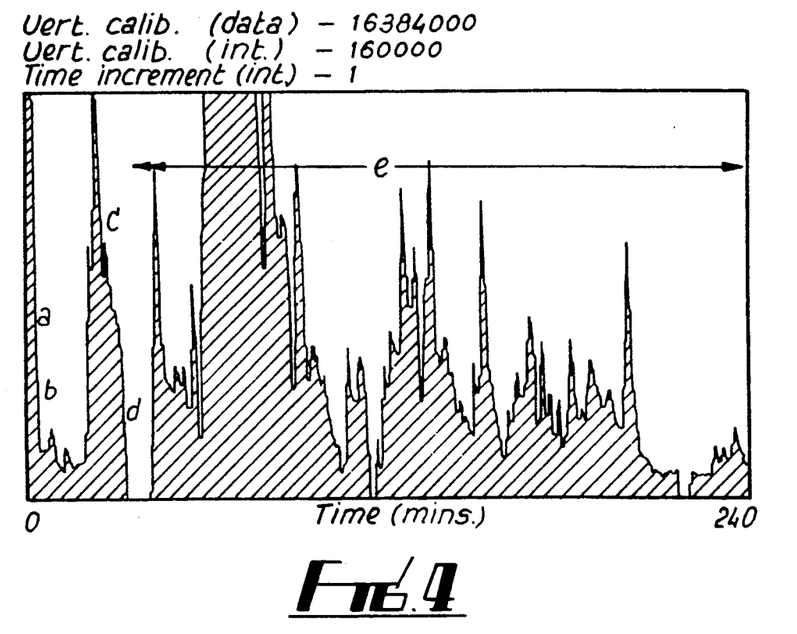

FIG. 4—Response to Drug Stimulation.

This tracing is from the same patient as in FIG. 3 and was taken after the same solid meal, but this time after stimulation with the drug cisapride.

a is the calibration signal, b the fasting phase, c the response to cisapride in the fasting phase (note that the response is immediate since the drug has been given intravenously), d a pause of 8 minutes for a meal, and e the response to cisapride in the fed phase i.e. after the solid meal.

Figure 5:
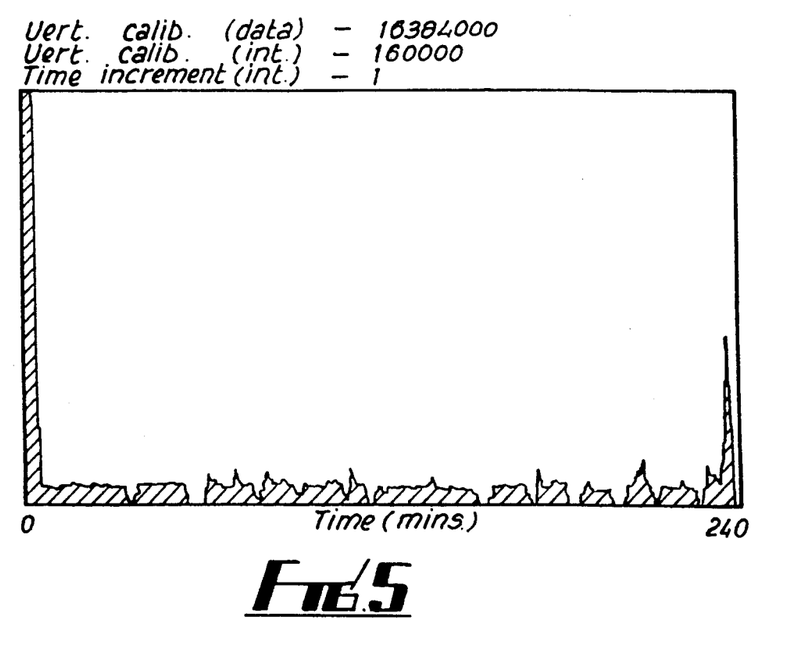

FIG. 5—Post Operative Ileus.

Note that the tracing is flat as would be expected. The stomach and bowel have "gone to sleep" after a recent operation and show no response to a meal, which has been given to the patient.

Figure 6:
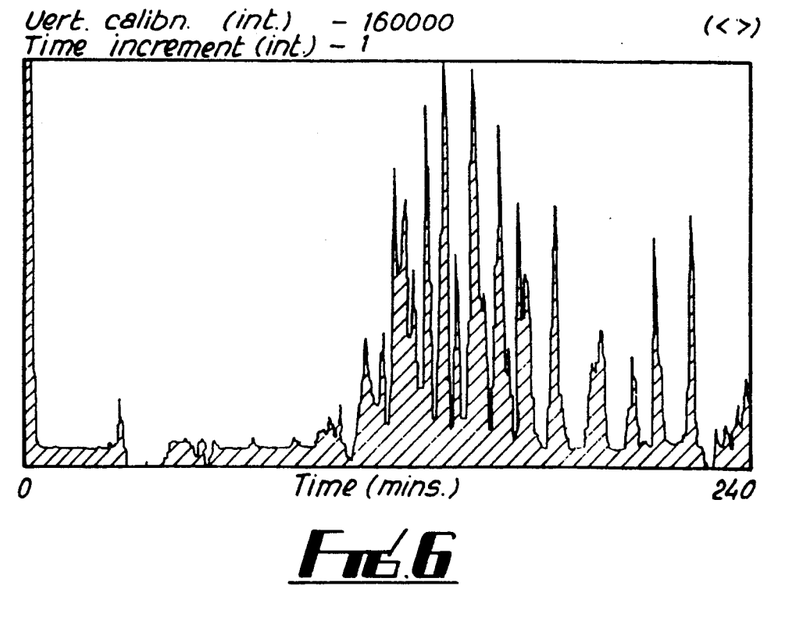

FIG. 6—Chronic Intestinal Obstruction.

a is the calibration signal, b the fasting phase, c a pause for a solid meal and d the response to the meal. The hiqh energy peaks which recur frequently and are tightly packed together are characteristic.

Figure 7:
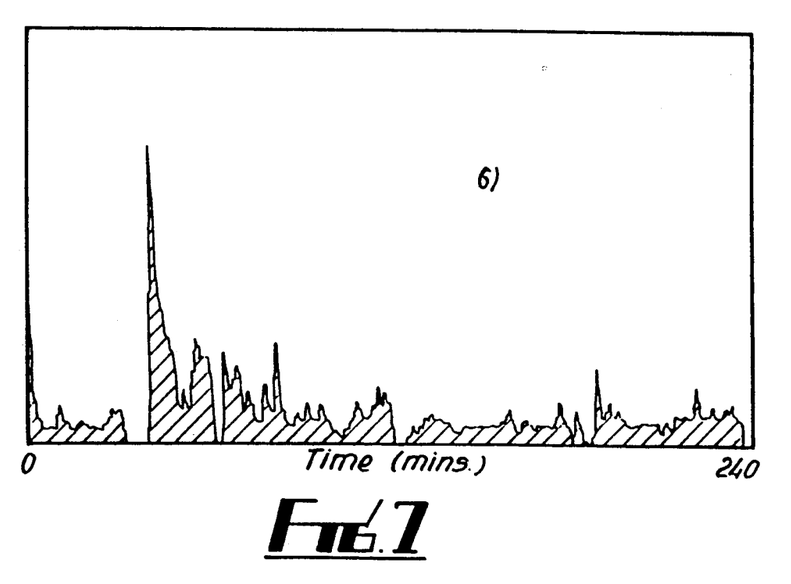

FIG. 7—Example of the Data Logging Capacity of the present method and apparatus. In this case the time intervals were of one minute duration.

Figure 8:
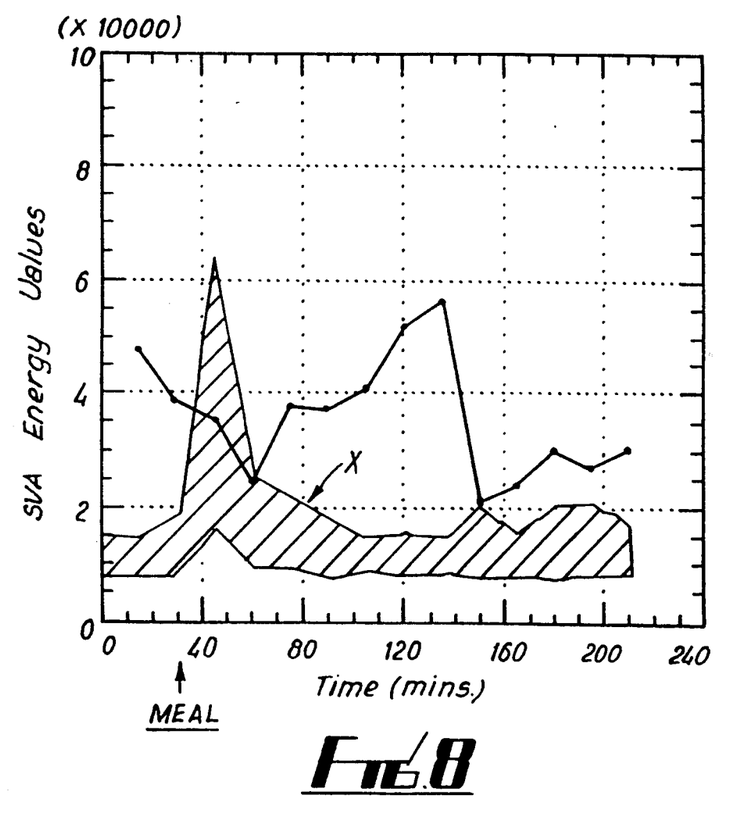
Figure 9:
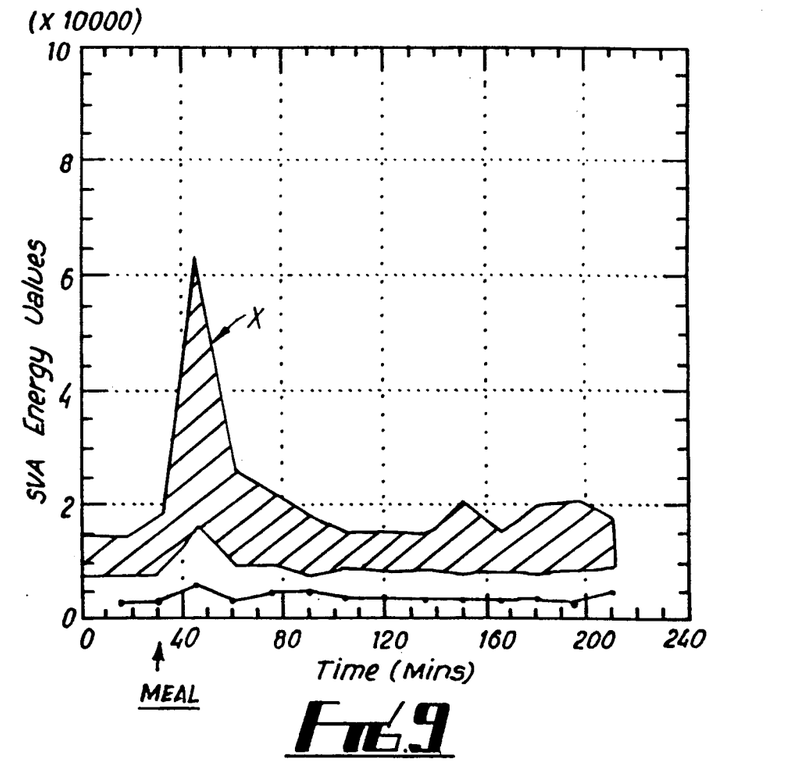

FIGS. 8-9—Response to a Solid Meal in Comparison with Normal Response.

These charts were obtained from patients having abnormal response. In FIG. 8 the chart shows late activity which is consistent with a blockage low down in the gastrointestinal tract, while in FIG. 9 the chart illustrates very low activity similar to that in FIG. 5. In each case the shaded area X has been printed on the chart paper to illustrate the normal reaction range, thus giving a rapid and easily-read indication of whether each patient's reaction is normal (within the area X) or abnormal (outside the area X).

The method and apparatus of this invention can be used not only to provide results from patients in response to meals and stimulation, but also to provide information on the natural quiescent state of the gastrointestinal tract. Thus, for example, gastric migrating motor complex (MMC) can be monitored and studies. The vibrational signal produced my MMC is of low amplitude, but it has been found that liquid can be administered to increase the amplitude without upsetting the fasting pattern of patients.

Modifications and improvements may be incorporated without departing from the scope of the invention.

What is claim is:

1. A method of detecting motility comprising (I) detecting vibrations of an external surface of an abdomen generated by gastrointestinal contractions by contacting the external surface directly with means for producing a signal from said vibrations, (II) producing a signal from the detected vibrations, and (III) analyzing the produced signal in order to detect motility.

2. A method of detecting motility as claimed in claim 1, wherein said means for producing a signal from said detected vibrations includes means for producing a signal from said detected vibrations having a frequency range extending beyond the acoustic spectrum and within the range 2 to 68,000 Hz.

3. A method of detecting motility as claimed in claim 1, wherein said method further includes the step of filtering out low frequencies from said detected vibrations.

4. A method of detecting motility as claimed in claim 1, wherein said produced signal is subjected to integration over discrete time intervals.

5. A method of detecting motility as claimed in claim 1, wherein said produced signal is amplified.

6. A method of generating data relating to motility, comprising (I) detecting vibrations of an external surface of an abdomen generated by gastrointestinal contractions by contacting the external surface directly with a means for producing a signal from said vibrations, (II) producing a signal from the detected vibrations, and (III) processing said signal to generate data relating to motility.

7. A method of generating, for use in diagnosis, data representing motility, comprising (1) providing a transducer operable, in response to physical vibration, to generate an electrical signal output, said vibration and said output having corresponding frequency components extending over and beyond both extremities of the acoustic frequency spectrum and applying said transducer in direct contact with the external surface of the abdominal wall of a patient to detect vibration of said wall caused by intestinal movements and generating an electrical signal output therefrom; and (2) processing said output to generate data representing motility.

8. A method as claimed in claim 7, comprising (1) maintaining application of said transducer to said surface for a period of time; and (2) compacting the electrical signal output resulting from said application by subjecting said output from successive short intervals during said period to a processing step, wherein said processing step is selected from a group of processes comprising summing, averaging and integrating.

* * * * *